(12) United States Patent
Celinska et al.

(10) Patent No.: US 6,495,709 B1
(45) Date of Patent: Dec. 17, 2002

(54) LIQUID PRECURSORS FOR ALUMINUM OXIDE AND METHOD MAKING SAME

(75) Inventors: Jolanta Celinska, Colorado Springs, CO (US); Jeffrey W. Bacon, Colorado Springs, CO (US); Akihiro Matsuda, Osaka (JP); Carlos A. Paz de Araujo, Colorado Springs, CO (US)

(73) Assignees: Symetrix Corporation, Colorado Springs, CO (US); Matsushita Electric Industrial Co., Ltd. (JP)

( * ) Notice: Subject to any disclaimer, the term of this patent is extended or adjusted under 35 U.S.C. 154(b) by 0 days.

(21) Appl. No.: 09/526,786

(22) Filed: Mar. 16, 2000

(51) Int. Cl.$^7$ ................................ C07F 5/06; C01F 7/02
(52) U.S. Cl. ..................... 556/183; 423/625; 423/628
(58) Field of Search ................... 556/183; 423/625, 423/628

(56) References Cited

U.S. PATENT DOCUMENTS

| | | | |
|---|---|---|---|
| 4,542,579 A | 9/1985 | Poponiak et al. | 29/576 W |
| 4,790,920 A | 12/1988 | Krzanich | 204/192.17 |
| 4,952,539 A * | 8/1990 | Greber et al. | 501/153 |
| 5,209,688 A | 5/1993 | Nishigaki et al. | 445/24 |
| 5,514,933 A | 5/1996 | Ward et al. | 313/582 |
| 5,559,260 A | 9/1996 | Scott et al. | 556/28 |
| 5,674,553 A | 10/1997 | Shinoda et al. | 427/68 |
| 5,739,180 A | 4/1998 | Taylor-Smith | 523/203 |
| 5,756,147 A | 5/1998 | Wu et al. | 427/66 |
| 5,783,483 A | 7/1998 | Gardner | 438/627 |
| 5,790,087 A | 8/1998 | Shigeta et al. | 345/67 |
| 5,840,465 A | 11/1998 | Kakinuma et al. | 430/270.1 |
| 5,877,734 A | 3/1999 | Amemiya | 345/60 |

FOREIGN PATENT DOCUMENTS

JP 60199896 * 10/1985

* cited by examiner

Primary Examiner—Porfirio Nazario-Gonzalez
(74) Attorney, Agent, or Firm—Patton Boggs LLP

(57) ABSTRACT

A precursor for forming an aluminum oxide film comprises a liquid solution of an aluminum organic precursor compound in an organic solvent. In a second embodiment, the precursor comprises a suspension of aluminum oxide powder in a solution of an aluminum organic precursor compound. A precursor according to the invention is deposited on a substrate by dipping, rolling, spraying, misted deposition, spin on deposition, or chemical vapor deposition then heated to fabricate transparent aluminum oxide films. The electronic properties of the aluminum oxide films may be improved by depositing a plurality of layers of the precursor and annealing the precursor between layers.

20 Claims, 8 Drawing Sheets

LIQUID PRECURSORS FOR ALUMINUM OXIDE AND METHOD MAKING SAME

BACKGROUND OF THE INVENTION

1. Field of the Invention

This invention relates to aluminum oxide layers in integrated circuits, fluorescent lamps, flat panel displays, and other electronic and electrooptical devices, and more particularly to nonaqueous organic precursors for making such aluminum oxides and methods for making such precursors and aluminum oxide layers.

2. Statement of the Problem

A fluorescent lamp typically comprises a cylindrical glass tube, or envelope, containing a fill gas of mercury vapor and a phosphor layer covering the inside of the tube wall. Often, a transparent conductive layer is located between the inner surface of the glass tube wall and the phosphor layer. A protective layer of aluminum oxide, often called alumina, is located between the conductive oxide layer and the phosphor layer to inhibit or delay discoloration and other appearance defects in the phosphor layer and the conductive oxide layer. A conventional technique of the art of forming transparent aluminum oxide layers in fluorescent lamps involves: dispersing a solid powder of aluminum oxide in a liquid medium to make a colloidal suspension of the oxide; applying a coating of the suspension onto a surface of the lamp; and drying the coating to form the aluminum oxide layer. Generally, it is difficult to achieve a uniform, continuous thin film by applying a colloidal suspension of powdered particles. Another technique involves dissolving a metal alkyl precursor compound in a solvent and spraying the precursor solution onto a hot surface having a temperature above the crystallization temperature of aluminum oxide, whereby the precursor compound is immediately pyrolyzed. It is generally difficult to form a uniform, continuous aluminum oxide thin film by the conventional pyrolysis method of the prior art because pyrolysis of the sprayed precursor compound on the hot substrate results in a broken, uneven surface on the microscopic level.

Transparent thick films of metal oxide are used as dielectric layers and buffer layers in flat panel displays. Using conventional techniques, it is difficult to achieve thick film layers having uniform thickness. In order to form a thick film layer that sufficiently adheres to the underlying substrate, it is necessary to form a coating from metal oxide powder and then heat the coating above the sintering temperature of the metal oxide. High process temperatures are usually incompatible with other materials commonly used in flat panel displays.

Thin films of aluminum oxide are formed in integrated circuits for use as protective "cap" layers, diffusion barrier layers, and dielectric insulators. An aluminum oxide capping layer formed on an underlying metal layer, such as aluminum or gold, protects the metal layer against "notches" and "mouse bites", which are caused during etching of the wafer during typical fabrication steps. Aluminum oxide also functions well as a diffusion barrier against high-performance metals, such as copper, gold, and silver, which can be used as metallization layers and local interconnects in integrated circuits. Aluminum oxide may be deposited on integrated circuit substrates to function as insulating layers and to fill insulator gaps and recesses. Very thin films of aluminum oxide function well as insulators and diffusion barriers. Thin films in the range of from 5 nm to 300 nm are typically desired in integrated circuits. Aluminum oxide adheres well to common semiconductor substrates, such as silicon and silicon oxide. Often a layer of aluminum is deposited, which is then oxidized by thermal oxidation. Anodization of aluminum using electrolytic solutions is also used in conventional processes. Aluminum oxide in integrated circuits is also commonly formed using sputtering and evaporation techniques. These conventional processes are complex and do not reliably produce structurally and chemically uniform aluminum oxide films.

For the above reasons, it would be very desirable to have a method of forming aluminum oxide that provides uniform thin and thick films without defects and with good electronic properties, and which lends itself to a commercial manufacturing environment.

SOLUTION

The present invention provides a method of forming an aluminum oxide thin or thick film utilizing a liquid precursor containing aluminum. The invention further provides novel nonaqueous organic precursors for forming aluminum oxide films, and methods of making such precursors. The invention may be used for forming aluminum oxide layers in an integrated circuit, a fluorescent lamp, a flat panel display or other electronic or electrooptical device.

One embodiment of the invention is a nonaqueous organic precursor comprising an aluminum organic liquid precursor solution ("precursor solution") for forming an aluminum oxide thin film layer. In this embodiment, the liquid precursor is a solution in which one or more aluminum organic precursor compounds are dissolved in one or more organic solvents. A liquid precursor solution of the invention is usually applied to a substrate surface using a liquid source deposition technique. The liquid precursor solution contains one or more aluminum organic precursor compounds that lead to formation of the desired aluminum oxide layer upon reaction and crystallization on the substrate surface. The precursor is applied to the substrate surface and treated, usually by one or more heating techniques. As a result, the organic precursor compound or compounds react to form a solid layer having the desired composition on the substrate surface.

A second embodiment of the invention is a nonaqueous organic precursor containing a suspension of aluminum oxide ("precursor suspension") for forming an aluminum oxide thick film layer. In this embodiment, the precursor suspension comprises both a suspension of aluminum oxide powder and an aluminum organic precursor solution. The aluminum oxide powder is suspended in an organic liquid medium. The aluminum organic solution includes one or more aluminum organic precursor compounds dissolved in one or more organic solvents. The organic liquid medium of the precursor suspension is selected to be identical with or soluble in the organic solvent of the aluminum organic solution. The aluminum oxide powder, the aluminum organic precursor solution, and the organic liquid are mixed to form an inventive precursor suspension. The resulting slurry of the precursor suspension provides a chemically stable, long-lived suspension suitable for depositing a coating on a substrate by screen printing or other thick film deposition methods. The aluminum organic precursor compound or compounds dissolved in the organic liquid medium of the precursor suspension are dispersed throughout the coating. The deposited coating is heated at relatively low temperatures, less than the sintering temperature of aluminum oxide. Thermal decomposition and reaction of the aluminum organic precursor compounds that permeate the aluminum oxide powder in the slurry coating result in formation of a homogeneous aluminum oxide solid thick film and interconnected uniformly homogeneous aluminum oxide solid thick film. The presence of organic compounds in the deposited coating that react to form aluminum oxide upon treating promotes necking which facilitates the low temperature formation of a continuous and highly cohesive phase of the solid. Without such necking, a continuous cohesive solid can be formed only by approaching or reaching the melting point of the solid. In addition, utilizing the prior art methods that start with a powder, significant voids remain in the solid even after sintering. The reaction of the organic compounds, on the other hand, results in a lesser number of voids, and, in fact, tends to fill any voids present, resulting in better breakdown strength as well as enhanced electrical and other physical properties. The necking also assists in adhering the aluminum oxide material to the underlying substrate.

A layer of aluminum oxide, in particular a thick film of aluminum oxide, is useful as a buffer layer in flat panel displays. A layer of aluminum oxide has a lower leakage current and a higher breakdown voltage than lead oxide having the same layer thickness. Thus, both thin film layers and thick film layers containing aluminum oxide are useful in flat panel displays, serving as insulators or protective coatings in the display. An inventive precursor suspension is especially useful for forming a thick film containing aluminum oxide because the aluminum organic precursor compounds in solution permeating the coating give rise to a homogeneous material and good adhesive "necking" to the substrate.

In the fabrication of an aluminum oxide layer, a substrate, such as a lamp envelope, may be dipped or rolled in liquid precursor to form a liquid coating of precursor, which is then treated; the liquid precursor solution may also be applied using a liquid spraying method, which is typically used in the fluorescent lamp art. In the fabrication of aluminum oxide thin film layers in integrated circuits, flat panel displays, fluorescent lamps and other electrooptical devices, an inventive liquid precursor solution may be applied by a liquid misted deposition method, in which a very fine mist of liquid particles is formed in a carrier gas and deposited on the substrate surface.

According to the invention, the liquid precursor solution or a precursor suspension is applied to the substrate surface, and then a solid metal oxide is formed in heating steps subsequent to the precursor application step. Electrical properties of an aluminum oxide film can be improved by adjusting the temperature and the duration of the heating steps.

Precursors according to the invention can be manufactured reliably. Their composition can be easily controlled and varied, if necessary. They are chemically stable, so they can be prepared in advance and stored safely for relatively long periods, up to six months. They are relatively nontoxic and nonvolatile, compared to precursors of the prior art. Metal oxide thin film layers formed using liquid precursors of the invention have smooth, continuous and uniform surfaces, especially compared to oxide layers of the prior art. They can be reliably fabricated to have thicknesses in the range of 5 nm to 1000 nm, maintaining important characteristics such as transparency and desired electrical properties.

Numerous other features, objects and advantages of the invention will become apparent from the following description when read in conjunction with the accompanying drawings.

DETAILED DESCRIPTION OF THE PREFERRED EMBODIMENT

1. Introduction

It should be understood that FIGS. 1–4, depicting fluorescent lamp, integrated circuit and flat panel display structures, are not meant to be actual plan or cross-sectional views of any particular portion of actual electronic devices.

In the actual devices, the layers may not be as regular and the thicknesses may have different proportions. The figures instead show idealized representations which are employed only to depict more clearly and fully the method of using the nonaqueous aluminum organic precursors of the invention than would otherwise be possible.

Figure 1:
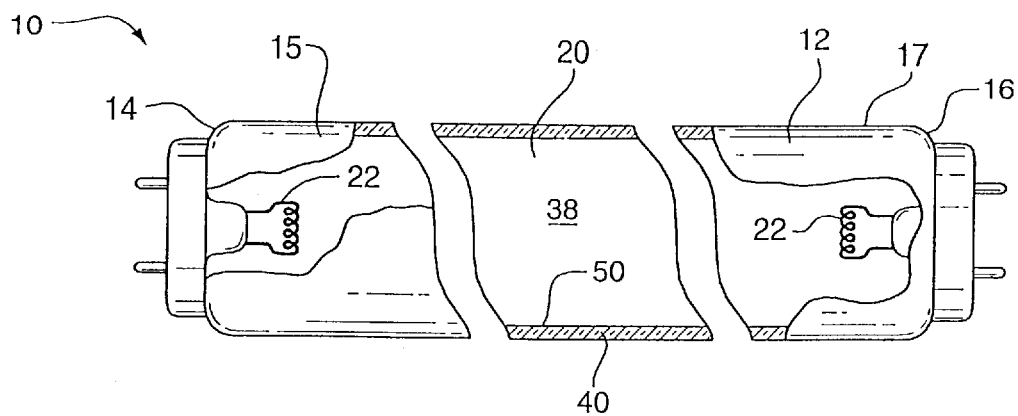
FIG. 1 shows a cross-sectional diagrammatic view of a finished fluorescent lamp 10 fabricated using a preferred embodiment of the inventive liquid precursor solution.
Figure 2:
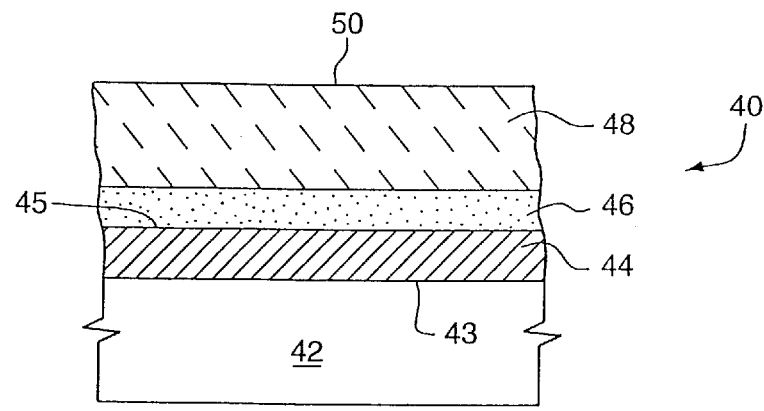
FIG. 2 shows an expanded view of the lamp wall of FIG. 1, including: an envelope wall; a conductive layer; a protective layer of $Al_2O_3$ in accordance with the invention; and a phosphor layer.

FIG. 1 shows a cross-sectional diagrammatic view of a finished fluorescent lamp 10 fabricated using a preferred embodiment of the inventive nonaqueous organic precursor. Fluorescent lamp 10 comprises an elongated, light-transmitting envelope 12. In the embodiment depicted in FIG. 1, envelope 12 is a cylindrical glass tube. Envelope 12 typically comprises soda glass, having a soda lime ($Na_2O$) content of 15% to 25%. Fluorescent lamp 10 has a lamp wall 40. As depicted in FIG. 2, lamp wall 40 comprises: an envelope wall 42 of envelope 12, having an inner envelope surface 43; a conductive layer 44; a protective layer 46; and a phosphor layer 48. Conductive layer 44 has a thickness in the range of 30 nm to 400 nm, preferably in the range of 60 nm to 80 nm. The inventive method and an inventive aluminum organic liquid precursor is used for forming protective layer 46 on conductive layer 44, as depicted in FIG. 2. Protective layer 46 comprises aluminum oxide, usually represented by the stoichiometric formula $Al_2O_3$. Protective layer 46 typically has a thickness in the range of from 20 nm to 200 nm, preferably about 100 nm.

Figure 3:
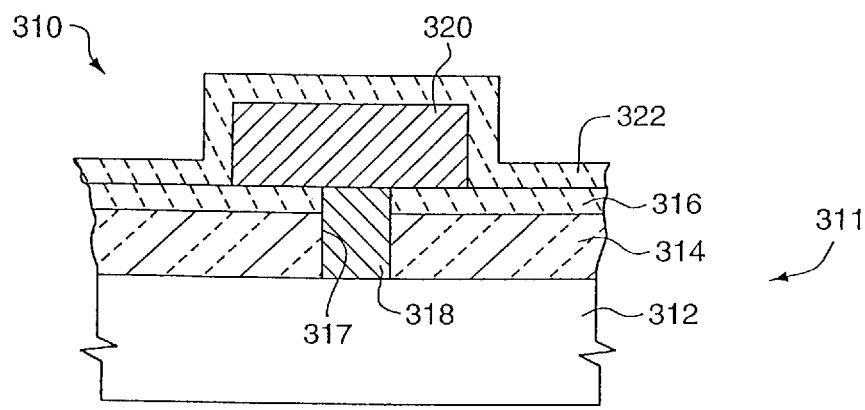
FIG. 3 depicts a representative integrated circuit section 310, fabricated in accordance with the invention.

FIG. 3 depicts a representative integrated circuit section 310, fabricated in accordance with the invention. Section 310 comprises a substrate wafer 311 containing a conventional semiconductor substrate 312. Typically, semiconductor substrate 312 comprises crystalline silicon, but may also comprise galium arsenide, silicon/germanium material or other semiconductor substrate material. Semiconductor substrate 312 also typically comprises a field oxide layer (not shown) and an integrated circuit device (not shown), for example, a field effect transistor. Semiconductor substrate 312 may further comprise additional structural layers and devices common to integrated circuits. Semiconductor substrate 312 is covered by interlayer dielectric layer ("ILD") 314, typically comprising a boron-doped phosphosilicate glass. ILD 314 is typically 400 nm to 1000 nm thick. ILD 314 is covered by aluminum oxide barrier layer 316, fabricated in accordance with the invention. Barrier layer 316 typically has a thickness in the range of from 5 nm to 300 nm, preferably about 30 nm. Electrically conductive plug 318, typically comprising polycrystalline silicon or tungsten, fills via 317 extending through ILD 314 and barrier layer 316. Metal layer 320 is disposed on barrier layer 316, over via 317, so that conductive plug 318 provides electrical connection between the bottom of metal layer 320 and semiconductor substrate 312, or other electronic element of integrated circuit 310. Metal layer 320 may be any metallized conductive material, preferably a high performance metal, such as copper, gold or silver. Barrier layer 316 provides a barrier against diffusion of metal atoms from metal layer 320 into semiconductor substrate 312 and other parts of the integrated circuit. Metal layer 320 is covered by aluminum oxide capping layer 322, fabricated in accordance with the invention. Capping layer 322 provides protection to metal layer 320 against "notches" and "mouse bites" during subsequent integrated circuit fabrication steps, as well as acting as a barrier against diffusion of metal atoms from metal layer 320 to other parts of the integrated circuit. Capping layer 322 typically has a thickness in the range of from 5 nm to 300 nm, preferably about 30 nm.

Figure 4:
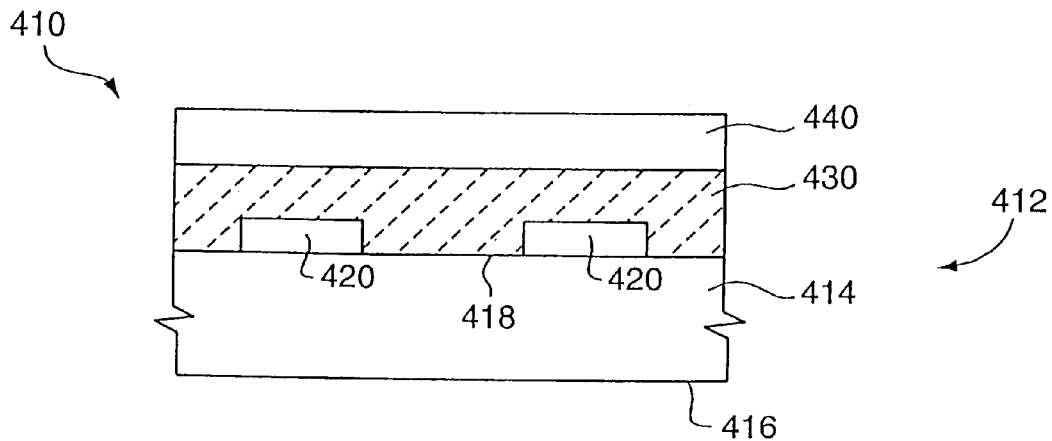
FIG. 4 depicts a front viewing panel of a representative flat panel display that includes a conventional soda-lime glass substrate, a dielectric glass layer containing aluminum oxide in accordance with the invention, and a magnesium oxide layer covering the dielectric layer.

FIG. 4 depicts representative flat panel display section 410, which is a portion of a front viewing panel 412 of a flat panel display. Front panel 412 includes a conventional soda-lime glass substrate 414 having a forward viewing surface 416 that is remote from interior surface 418. Interior surface 418 supports a plurality of cathodes 420, fabricated using conventional means. A dielectric glass layer 430 is deposited over interior surface 418. Dielectric glass layer 430 separates and insulates the respective cathodes. Dielectric glass layer 430, fabricated in accordance with the invention, comprises aluminum oxide and has a thickness in the range of from 1 μm to 40 μm, preferably 10 μm. A magnesium oxide layer 440 covers dielectric glass layer 430. Magnesium oxide layer 440 lowers the voltage that is required to drive the flat panel display, and eliminates erosion of dielectric glass layer 430.

The term "thin film" as used herein generally means a film of less than a micron in thickness. The thin films disclosed herein are in all instances less than 1.0 micron in thickness. Typically, the metal oxide thin film layers of the invention have a thickness in the range of from 20 nm to 500 nm, preferably in the range of from 20 nm to 200 nm. The term "thick film" as used herein generally means a layer having a thickness of 1.0 micron or more.

2. Precursor Composition and Formation of Aluminum Oxide

The word "precursor" used herein with reference to the invention may refer to two embodiments of the invention, both of which contain an aluminum organic precursor compound dissolved in organic solvent. A nonaqueous organic precursor for making a thin film, designated herein as a "precursor solution", contains an aluminum organic precursor compound dissolved in organic solvent. A precursor for making a thick film, designated by the term "precursor suspension", refers to a mixture that likewise contains an aluminum organic precursor compound dissolved in organic solvent, but which also contains aluminum oxide powder suspended in organic liquid. The composition of a precursor may be described in various ways. The actual dissolved or suspended aluminum-containing organic compounds and their concentrations may be specified; the relative molar proportions of chemical elements in the precursor may be specified; or the stoichiometric formula representing the composition of the final aluminum oxide material to be formed with the precursor may be specified. Those skilled in the art understand all three methods of description.

The term "stoichiometric" herein may be applied to both a solid layer of a material or to the precursor for forming a material. When it is applied to a solid layer, it refers to a formula which shows the actual relative amounts of each metal element in a final solid layer. When applied to a precursor, it usually indicates the molar proportion of metals in the precursor.

Terms of orientation herein, such as "above", "top", "upper", "below", "bottom" and "lower" are relative terms, explained here by reference to FIGS. 2 and 3. In FIG. 2, the terms are interpreted relative to envelope wall 42. That is, if a second element is "above" a first element, it means the second element is farther from envelope wall 42; and if it is "below" another element, then it is closer to envelope wall 42 than the other element. The long dimension of a fluorescent lamp defines the axial and horizontal direction. In FIG. 3, the terms of orientation are relative to substrate 312. The long dimension of substrate 312 in FIG. 3, i.e., the horizontal direction in the figure, is considered to be the "horizontal" direction. If an element is "above" another element, then it is farther from substrate 312. For example, metal layer 320 is above barrier layer 316. Terms such as "above" and "below" do not, by themselves, signify direct contact. However, terms such as "on" or "onto" usually do signify direct contact of a layer with a contiguous layer.

The term "substrate" is sometimes used ambiguously. It can refer to the original starting material on which layers and device elements are formed, such as envelope wall 42 of FIG. 2 or substrate 312 in FIG. 3. It may also have the general meaning of any object or surface on which a material layer is directly deposited. For example, in FIG. 2, conductive layer 44 is the substrate on which protective layer 46 is deposited. In this disclosure, "substrate" or "substrate surface" shall generally mean the surface on which a precursor is applied or a layer of material is deposited.

Terms such as "heating", "distilling", "drying", "baking", "rapid thermal process" ("RTP"), "annealing", and others all involve the application of heat. For the sake of clarity, the various terms are used to distinguish certain techniques and method steps from one another. Nevertheless, it is clear that similar techniques may be used to accomplish differently named process steps; for example, drying, baking and annealing may typically be accomplished using the same apparatus, the only differences being their function and position in a fabrication sequence, or the particular temperatures used. As a result, it would be possible to designate an annealing step as a heating step, or a drying step as a baking step. To avoid confusion, therefore, the general term "heating" may also be used to describe a fabrication step, especially in the claims describing the invention. It is further understood that one skilled in the art may accomplish a desired process result using heating as disclosed herein, while referring to the process with a term different from the one used herein.

A precursor solution is typically formed by mixing an alkoxide of aluminum with a carboxylic acid, or with a carboxylic acid and an alcohol, and conducting chemical reactions in a solvent. Metal alkoxides may be selected from a group including methoxides, ethoxides, isopropoxides, n-butoxides and pentoxides. Carboxylic acids that may be used include 2-ethylhexanoic acid, octanoic acid, and neo-decanoic acid, preferably 2-ethylhexanoic acid. Alcohols that may be used include 2-methoxyethanol, 1-butanol, 1-pentanol, 2-pentanol, 1-hexanol, 2-hexanol, 3-hexanol, 2-ethyl-1-butanol, 2-ethoxyethanol, and 2-methyl-1-pentanol, preferably 2-methoxyethanol. Solvents that may be used include xylenes, n-octane, 2-methoxyethanol, n-butyl acetate, 1,4-dioxane, methanol, methyl ethyl ketone, n-dimethylformamide, 2-methoxyethyl acetate, methyl isobutyl ketone, methyl isoamyl ketone, isoamyl alcohol, cyclohexanone, 2-ethoxyethanol, 2-methoxyethyl ether, methyl butyl ketone, hexyl alcohol, 2-pentanol, ethyl butyrate, nitroethane, pyrimidine, 1,3,5-trioxane, isobutyl isobutyrate, isobutyl propionate, propyl propionate, ethyl lactate, n-butanol, n-pentanol, 3-pentanol, toluene, ethylbenzene, 1-butanol, 1-pentanol, 2-pentanol, 1-hexanol, 2-hexanol, 3-hexanol, 2-ethyl-1-butanol, 2-ethoxyethanol, and 2-methyl-1-pentanol, as well as many others. The metal, metal alkoxide, acid, and alcohol react to form a mixture of metal-alkoxocarboxylate, metal-carboxylate and/or metal-alkoxide, which mixture is heated and stirred as necessary to form metal-oxygen-metal bonds and boil off any low-boiling point organics that are produced by the reaction. The alcohol is preferably 2-methoxyethanol or 2-methoxypropanol. The carboxylic acid is preferably 2-ethylhexanoic acid. The reaction is preferably conducted in a xylenes or n-octane solvent. The reaction in the mixture is usually conducted in a nitrogen atmosphere. The reaction may be conducted at room temperature by stirring the mixture for a time period of from 6 hours to 48 hours. It is often preferable to heat the mixture at a temperature in the range of from 30° C. to 200° C. to enhance the reaction. The reaction is typically conducted using a reflux condenser. To remove water and volatile organics after reaction, the reaction mixture is heated using a distillation column at a temperature from 50° C. to 200° C. Liquid precursors of the invention are typically made in batches prior to their use. The solution is mixed to substantial homogeneity, and is preferably stored under an inert atmosphere of desiccated nitrogen or argon if the final solution will not be consumed within several days or weeks. This precaution in storage serves to assure that the solutions are kept essentially water-free and avoids the deleterious effects of water-induced polymerization, viscous gelling, and precipitation of metal atoms that water can induce in alkoxide ligands. Even so, the desiccated inert storage precaution is not strictly necessary when the precursor, as is preferred, primarily consists of metals bonded to carboxylate ligands and alkoxycarboxylates. The inventive liquid precursors are prepared to be stable so that they have a relatively long shelf-life, at least between two and six months' duration. Refrigeration of an inventive precursor may extend its shelf life. The stability of the precursors contributes to cost-efficiency and uniformity among production runs.

Immediately before application of a liquid precursor to a substrate surface, final preparation steps may be conducted, including mixing, solvent exchange, and dilution. A liquid precursor is typically diluted to a concentration of from 0.1 moles to 0.5 moles of the aluminum organic precursor compound per liter of solution. The precursor mixing, distillation, solvent control, and concentration control steps can be combined and/or ordered differently depending on the particular liquids used, whether one intends to store the precursor or use it immediately, and other considerations. For example, distillation is useful for removing unwanted by-products, as well as usually being part of solvent concentration control, and thus both functions are often done together. As another example, mixing and solvent control often share the same physical operation, such as adding particular reactants and solvents to the precursor solution in a predetermined order. Any of these steps of mixing, distilling, and solvent and concentration control may be repeated several times during the total process of preparing a liquid precursor solution.

The present invention provides novel liquid precursor solutions to make aluminum oxide thin films, particularly transparent aluminum oxide thin films. The inventive liquid precursor solutions permit the formation of aluminum oxide thin films through a low-temperature anneal process. The low-temperature anneal enables the widespread use of these materials in integrated circuits, flat panel displays and other electrooptical devices in which the other materials and the electronics of the device preclude high-temperature fabrication steps.

For liquid deposition methods, such as misted deposition and spin-on techniques, the preferred inventive precursor for depositing a metal oxide thin film is a nonaqueous aluminum organic liquid precursor solution in which a solvent comprises xylenes, n-octane or n-butyl acetate, and a metal organic precursor compound is aluminum ethylhexanoate. When a liquid precursor is prepared and stored for longer than one day, the solvent preferably comprises xylenes or n-octane only, and the liquid precursor has a concentration of approximately 0.5 molar. When the solution is about to be used, preferably it is diluted with n-octane or n-butyl acetate to about 0.2 molar concentration before application to a substrate.

Figure 5:
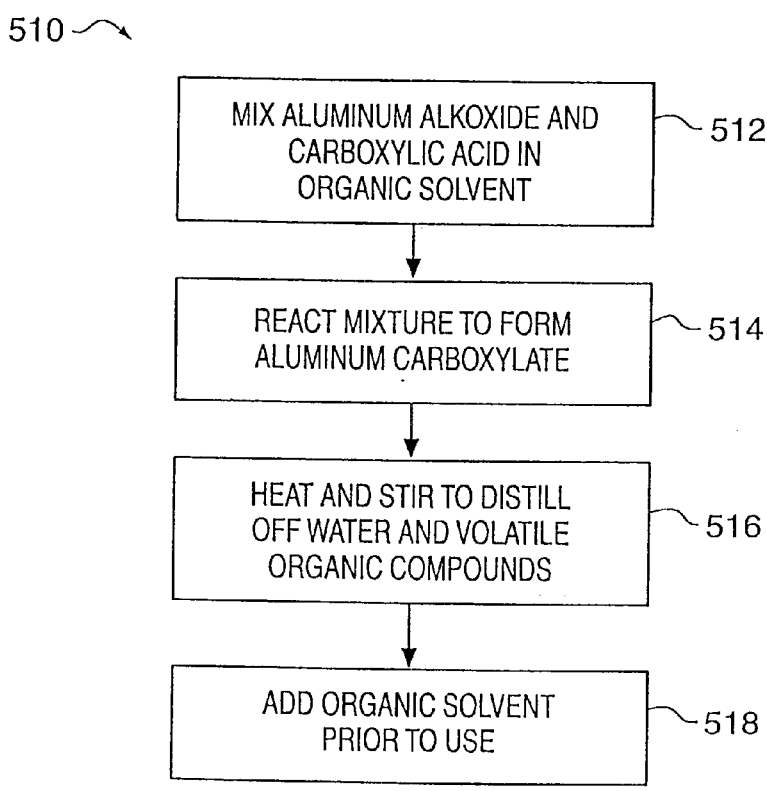
FIG. 5 depicts a flow chart of a preferred method for forming a liquid precursor solution according to the invention.

FIG. 5 depicts a flow chart of the preferred generalized method for forming a liquid precursor solution according to the invention. In step 512, an aluminum alkoxide is mixed with a carboxylic acid in an organic solvent. Preferably, the carboxylic acid is 2-ethylhexanoic acid, and the organic solvent is n-octane. In step 514, the mixture is reacted to form an aluminum alkoxycarboxylate, preferably aluminum 2-ethylhexanoate. Reaction is accomplished by stirring for 24 hours in a nitrogen atmosphere, or by heating with reflux at about 100° C. in a nitrogen atmosphere for about 24 hours, as described in the examples below. In step 516, the solution containing the aluminum alkoxycarboxylate is distilled at about 70° C. to 80° C. until the head temperature falls to below 50° C., and then the solution is cooled in a nitrogen atmosphere. Step 516 serves to boil off any water and any volatile organic compounds that are produced by the reaction. Preferably, at least 50% of the aluminum-to-oxygen bonds of the final aluminum oxide desired in the thin film are formed by the end of this step. When a desired aluminum carboxylate, or other aluminum organic precursor compound, of suitable quality is commercially available, then the metal carboxylate or other type of precursor compound may be purchased instead of forming it as outlined in steps 512–516. In step 518, usually immediately prior to use, organic solvent is added to the final precursor to adjust it to the desired concentration for deposition, usually about 0.2 molar.

Figure 6:
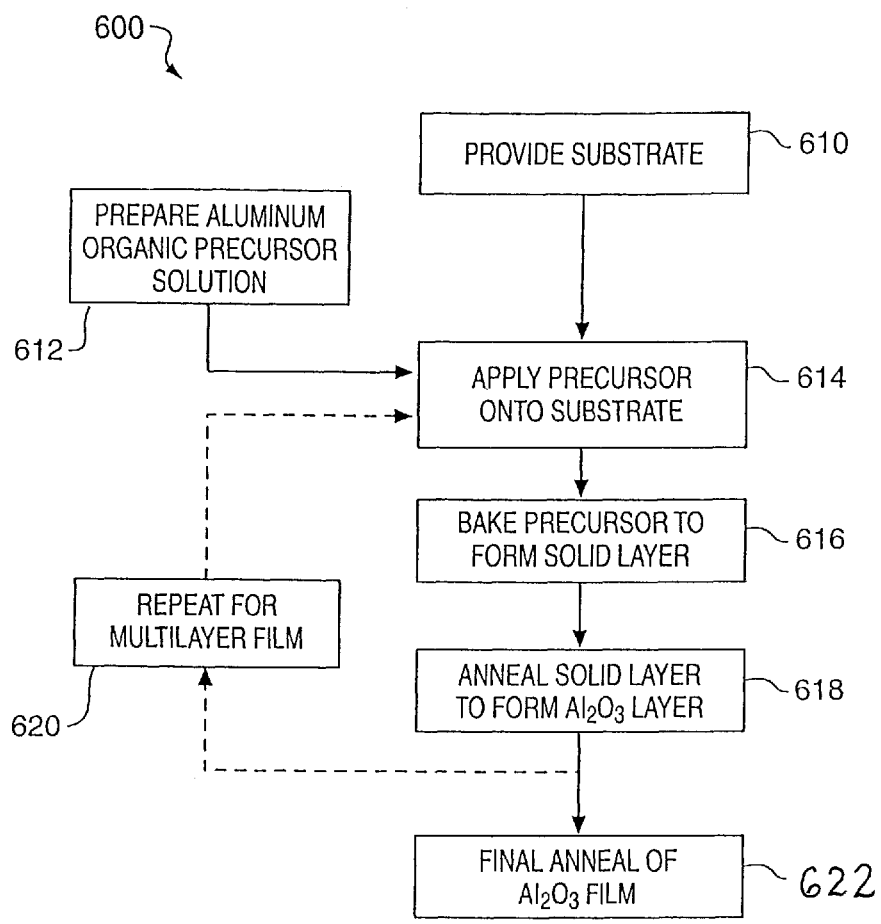
FIG. 6 is a flow chart showing the steps of a preferred liquid source deposition process for fabricating an aluminum oxide thin film in accordance with the invention.

FIG. 6 is a flow chart showing the steps of a liquid source deposition process 600 for fabricating an aluminum oxide thin film in accordance with the invention. The process is useful for fabricating aluminum oxide thin films in integrated circuits, fluorescent lamps, flat panel displays and other electronic and electrooptical devices. In step 610, a substrate is provided. As examples, the substrate may be: a conventional fluorescent lamp envelope 12 having conductive layer 44, as in FIG. 2; an integrated circuit portion having an ILD 314, as in FIG. 3; a flat panel display; or another device in which aluminum oxide thin film layers are used. In step 612, a liquid precursor solution for the aluminum oxide thin film is prepared. In step 614, the liquid precursor is applied onto the substrate using any deposition process suitable for nonaqueous metal organic liquid precursors. In the case of a protective layer in a fluorescent lamp, preferably a conventional liquid-source spraying method of the fluorescent lamp art is used, except that the liquid is an inventive liquid precursor solution rather than a colloidal suspension of the prior art. A liquid-source misted deposition process may also be used. In a misted deposition process, a mist comprising fine liquid particles suspended in a carrier gas is flowed through the interior space of the lamp envelope, where the liquid particles deposit on the surface of conductive layer 44. A misted deposition process has several advantages over a spraying process, including: better control over layer thickness and uniformity; less wasted precursor; continuous operation. Or the liquid precursor may be applied by rolling the envelope with liquid precursor in its interior space. Preferably, a cold envelope method, sometimes called a cold-tube method, is used. In a typical cold envelope technique, the inner lamp wall surface is not heated; rather, it is approximately at room temperature when the liquid precursor is applied to it. A liquid source misted deposition process is preferred for fabricating aluminum oxide thin films in integrated circuits and flat panel displays.

After the liquid precursor solution is applied in step 614, the substrate is treated to form aluminum oxide. Treating may comprise a process selected from the group including: exposing to vacuum, drying, heating, baking, rapid thermal processing, and annealing. In the preferred method, treatment includes baking and annealing. In step 616, baking serves to remove the organic solvent from the substrate and causes the aluminum organic precursor compound of the precursor to decompose and react. Baking is typically performed for one minute at 160° C., then at 260° C. for four minutes. In step 618, the solid layer is annealed. In step 618, a furnace anneal in an oxygen-containing atmosphere results in crystallization or recrystallization of the aluminum oxide. The oxygen-containing atmosphere typically is all oxygen gas, but may also be air or other mixture with at least one percent oxygen by volume. The annealing is conducted at a temperature in the range of from 400° C. to 600° C., for a duration of from 5 minutes to 60 minutes, preferably for about 30 minutes. The temperature and duration of the annealing affects the leakage current, breakdown voltage and other electrical properties of the aluminum oxide film. In fluorescent lamp manufacturing, usually only one coating of precursor is applied and treated. In integrated circuit and flat panel display manufacturing, a plurality of layers of aluminum oxide may be deposited to form a final thin film. This is represented in FIG. 6 by the dashed line associated with step 620, according to which steps 614 through 618 are repeated one or more times. It is preferred to perform anneal step 618 for each layer formed in step 616, but anneal step 618 may alternatively be skipped. In step 622, a final anneal step is conducted after the last layer of precursor has been applied and treated in steps 614–618. The final anneal is typically at a temperature in the range of from 400° C. to 600° C., preferably at 520° C.

Preferably, the precursor solution prepared in step 612 comprises a 0.20 molar solution of aluminum 2-ethylhexanoate in 2-ethylhexanoic acid and n-octane, as described in Example 1, below, for forming $Al_2O_3$.

In an alternative method, a liquid-source chemical vapor deposition ("LSCVD") method may be used to apply the liquid precursor by vaporizing either a single final precursor or several liquid precursor solutions in a carrier gas and flowing the vaporized precursor into a CVD reactor chamber, where the organic precursor compounds react to form a solid thin film layer, which is then annealed. Here, "vapor" refers to a gasified precursor.

Preferably, an LS-MCD method is used to make a very thin film having a thickness in the range of from 5 nm to 100 nm. A misted deposition process has several advantages over other techniques, including: better control over layer thickness and uniformity; less wasted precursor; continuous operation. Preferably, a 0.20 molar precursor solution of aluminum 2-ethylhexanoate in 2-ethylhexanoic acid and n-octane is prepared, as described in Example 1, below, for forming $Al_2O_3$. The integrated circuit wafer is placed in a misted deposition chamber, in which a liquid coating of the precursor solution is applied using known techniques. After application of the liquid precursor to form a liquid coating, the substrate wafer is baked, and then annealed. Baking is typically performed for one minute at 160° C., then at 260° C. for four minutes. In step 618, a furnace anneal in an oxygen-containing atmosphere, results in crystallization or recrystallization of the aluminum oxide. The oxygen-containing atmosphere typically is all oxygen gas, but may also be air or other mixture with at least one percent oxygen by volume. The annealing is conducted at a temperature in the range of from 500° C. to 600° C.

Figure 7:
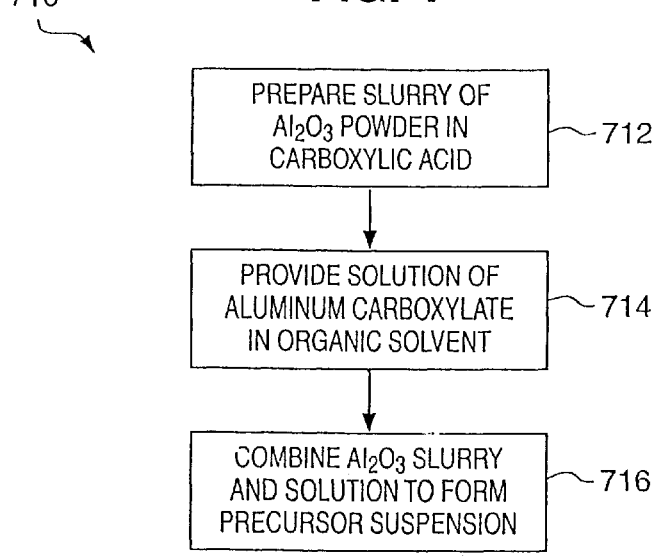
FIG. 7 depicts a flow chart of a preferred method for forming a precursor suspension in accordance with the invention.

FIG. 7 depicts a flow chart of the preferred method 710 for forming a precursor suspension according to the invention. In step 712, a slurry is prepared by mixing aluminum oxide powder with a carboxylic acid. Preferably, the carboxylic acid is ethylhexanoic acid. Preferably, 1 weight-part of $Al_2O_3$-powder is mixed with 3 weight-parts of ethylhexanoic acid. In step 714, a solution of an aluminum organic precursor compound in organic solvent is provided. Preferably, the solution comprises n-octane solvent. Preferably, the aluminum oxide precursor compound in the solution is aluminum 2-ethylhexanoate. Preferably, a 0.5 molar solution is used. In step 716, the slurry is mixed with the solution to form the precursor suspension.

The inventive precursor suspension is suitable for forming aluminum oxide thick films, having a thickness in the range of from 1 μm to 50 μm. The inventive precursor suspension is especially useful for forming transparent aluminum oxide thick films in flat panel displays.

EXAMPLE 1

An inventive nonaqueous organic precursor comprising a 0.5 molar liquid precursor solution for an aluminum oxide thin film layer was prepared by converting aluminum n-butoxide to aluminum 2-ethylhexanoate. Aluminum n-butoxide was obtained from Strem Chemicals, Inc. A 100 ml round-bottom flask was purged with nitrogen. 12 grams of aluminum n-butoxide was combined with 4.2 equivalents of 2-ethylhexanoic acid from Aldrich Company and 20 ml anhydrous n-octane in the round-bottom flask, which was purged with nitrogen again and connected to a reflux condenser. A slow flow of nitrogen was established into and out of the top of the condenser, and the flask was heated at 100° C. in an oil bath while the contents of the flask were stirred with a magnetic stirrer. After 18 hours, the flask was removed from the heat, the reflux condenser was disassembled, and the flask was purged again with nitrogen gas. The n-octane was added to a total volume of approximately 85 ml while the solution was still hot to prevent gelation. The solution in the flask was allowed to cool to room temperature. The cooled solution was poured into a graduated cylinder and n-octane was added to adjust the concentration to exactly 0.50 molar (approximately 100 ml). The 0.5 molar solution was filtered through a 0.2 micron filter and bottled.

The amounts of reactants and solvents used in Example 1 may be scaled up for commercial fabrication. For reasons related to safety and handling, it is preferable to use n-octane solvent instead of xylenes in commercial-scale processes.

EXAMPLE 2

An inventive nonaqueous organic precursor comprising a precursor suspension for forming a thick film of aluminum oxide was prepared by adding a slurry of aluminum oxide powder to a precursor solution as described above.

A 0.01–0.02 micron powder of aluminum oxide was obtained from Strem Chemicals, Inc. In a 100 ml beaker, 5 grams of aluminum oxide powder was combined with 15 grams of 2-ethylhexanoic acid and stirred with a glass rod until smooth and homogeneous. Then an equal volume of 0.5 molar precursor solution, as prepared in Example 1, was added to the mixture, which was then stirred with a glass rod until homogeneous.

EXAMPLE 3

Thin films of aluminum oxide of various thicknesses were formed on a series of thermally grown 0.15 μm silicon dioxide wafers using a precursor solution obtained from Kojundo Chemical Corporation comprising 0.5 molar solution of $Al_2O_3$ in xylenes. The thickness and leakage current in the various thin films were measured and compared.

To make each exemplary aluminum oxide thin film, a spin-on technique was used. A few drops of the 0.5 molar precursor were placed on a wafer, which was spun at 100 rpm for 5 seconds, then at 1500 rpm for 30 seconds. The wafer was soft baked at 150° C. to 160° C. for one minute, and hard baked at 260° C. for four minutes to form a first layer of solid film. The film was annealed at 350° C. for 5 minutes in $O_2$ gas flowing at 5 liter/min, with 10 minute push-pull. Then, using the same procedure on selected wafers, second, third, fourth and fifth layers were variously applied, including the anneal at 350° C. before applying the next layer, except that a final anneal of each wafer was performed at 600° C. after the final layer was baked. After the final (second, third, fourth or fifth) layer was applied and the final anneal performed at 600° C., film thickness, film leakage current, breakdown voltage and crystallographic x-ray measurements were conducted. Breakdown strength values were calculated from the breakdown voltage. The measured thickness of a thin film with two layers was about 130 nm; with three layers, 180 nm; with four layers, 220 nm; and, with five layers, 260 nm.

Figure 8:
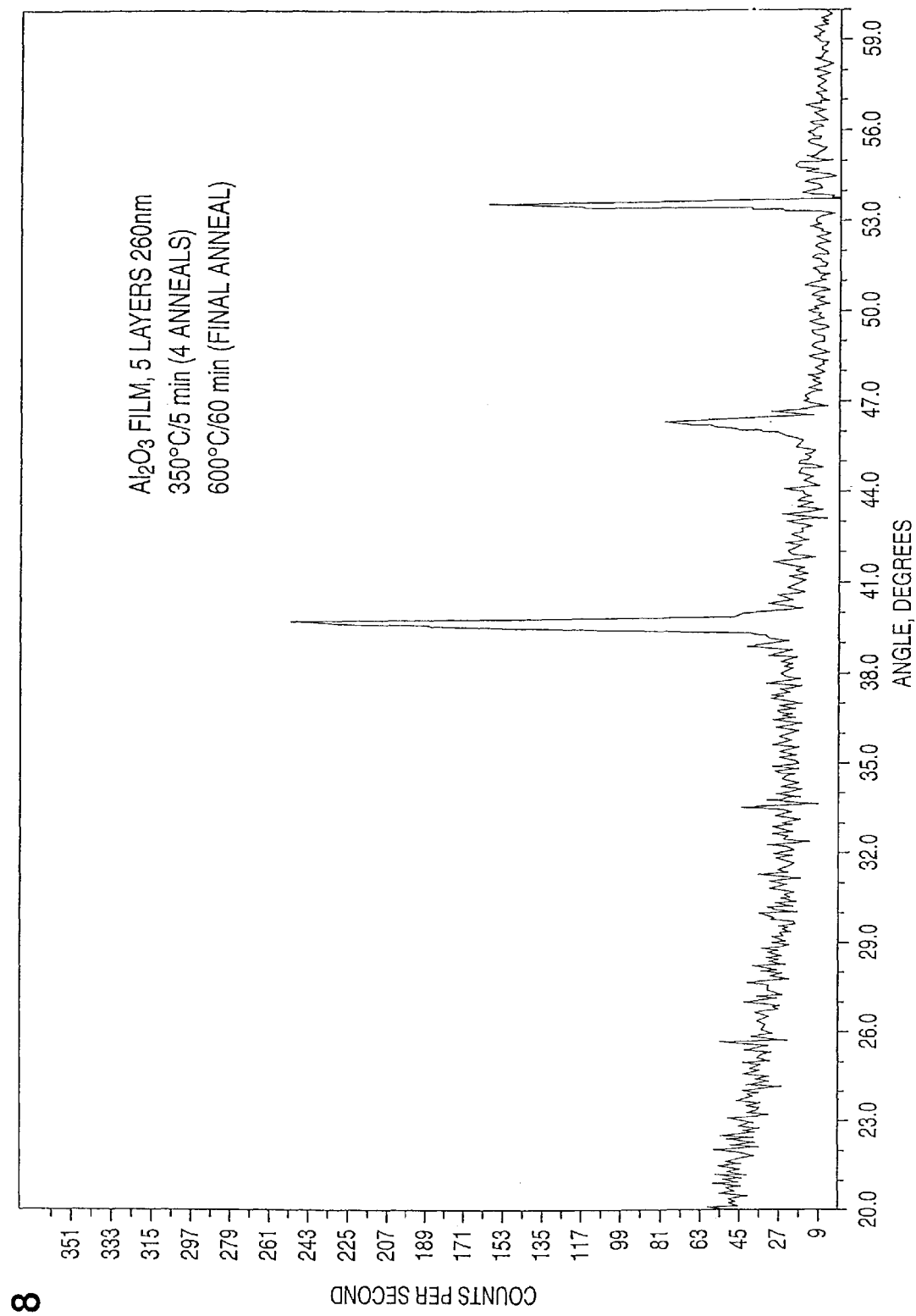
FIG. 8 depicts the results of a crystallographic x-ray analysis of an aluminum oxide thin film formed by annealing for 5 minutes at 350° C. between spin-on layers, with a final anneal at 600° C. for 60 minutes.
Figure 9:
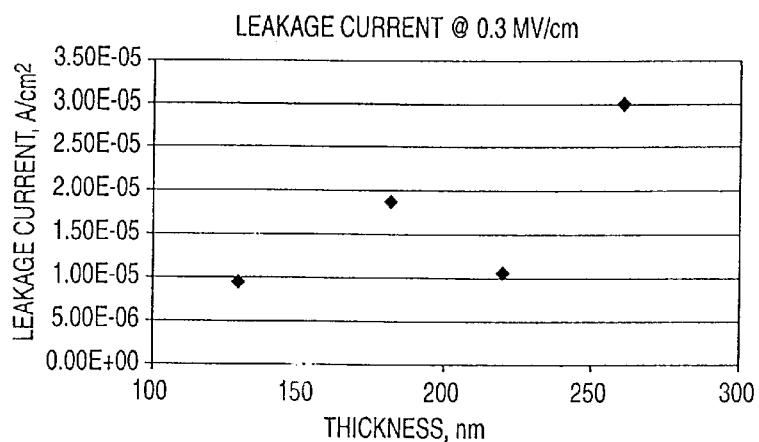
FIG. 9 is a graph of leakage current in units of $A/cm^2$, measured at 0.3 MV/cm and plotted as a function of film thickness, in nanometers, in the thin film of FIG. 8.
Figure 10:
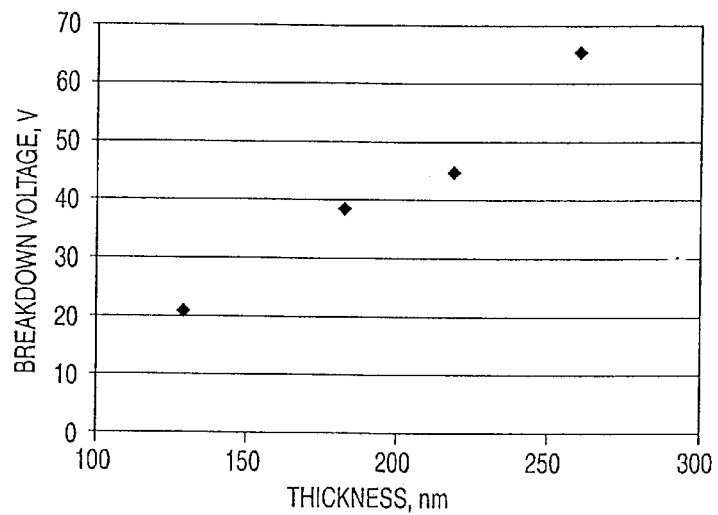
FIG. 10 is a graph of breakdown voltage, in volts, plotted as a function of film thickness, measured in the thin film of FIGS. 8 and 9.
Figure 11:
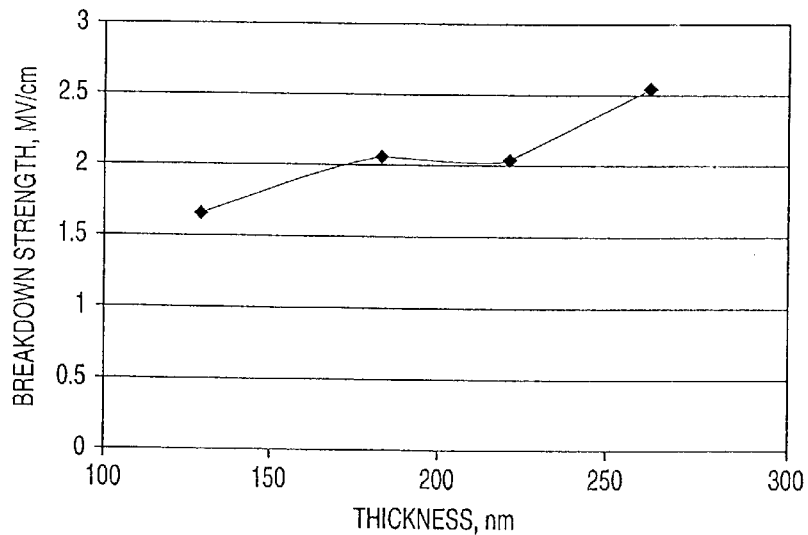
FIG. 11 is a graph of breakdown strength, in MV/cm, plotted as a function of film thickness, in the thin film of FIGS. 8–10.

FIG. 8 depicts the results of a crystallographic x-ray analysis of an aluminum oxide thin film having five layers after the final anneal at 600° C. plotted as counts per second versus angle in degrees. FIG. 9 is a graph of leakage current in units of $A/cm^2$, measured at 0.3 MV/cm and plotted as a function of film thickness, in nanometers. FIG. 9 shows that the leakage current tends to increase with increasing film thickness, and that the leakage current was $3.0 \times 10^{-5}$ $A/cm^2$ in the thin film having five layers and a thickness of 260 nm after the final anneal at 600° C., measured at a field strength of 0.3 megavolts ("MV") per centimeter, typical of plasma display panels. In FIG. 10, breakdown voltage, in volts, is plotted as a function of film thickness. The data in FIG. 10 indicate that breakdown voltage increased with film thickness, and it had a value of 67.7 volts at 260 nm. The data in FIG. 10 was converted to values of breakdown strength, in MV/cm, and plotted as a function of film thickness in the graph of FIG. 11. The breakdown strength increased with film thickness and had a value of 2.5 MV/cm at 260 nm.

EXAMPLE 4

Thin films of aluminum oxide were formed on a series of thermally grown 0.15 μm silicon dioxide wafers using a precursor solution obtained from Kojundo Chemical Corporation comprising 0.5 molar solution of $Al_2O_3$ in xylenes, as in Example 3. In a first group of wafers, no annealing was performed between layers. In a second group, annealing was performed between layers, but the annealing temperature used between layers was increased from 350° C. of Example 3 to 520° C., and the anneal time increased from 5 minutes to 30 minutes. The temperature of the final anneal for both groups was lowered from 600° C. to 520° C.

To make each exemplary aluminum oxide thin film, a spin-on technique was used. A few drops of the 0.5 molar precursor were placed on each wafer from two groups of wafers. The wafer was spun at 500 rpm for 5 seconds, then at 1500 rpm for 30 seconds. The wafer was soft baked at 160° C. for one minute, and hard baked at 260° C. for four minutes to form a first layer of solid film.

In the first group of "bake-only" wafers, using the same procedure, second, third, fourth and fifth layers were variously applied, and a final anneal of the wafer at 520° C. was performed after the final (second, third, or fifth) layer was baked. The final anneal at 520° C. was conducted for 60 minutes in $O_2$ gas flowing at 5 liter/min, with 10 minute push-pull In the second group of "anneal between layers" wafers, the first layer film was annealed at 520° C. for 30 minutes in $O_2$ gas flowing at 5 liter/min, with 10 minute push-pull. Then, using the same procedure on selected wafers, second, third, fourth and fifth layers were variously applied, including the anneal at 520° C., before applying the next layer. After the final (second, third, or fifth) layer was applied and baked, a final anneal of the wafer at 520° C. for 60 minutes was performed. After the final layer was applied and the final anneal performed at 520° C., film thickness, film leakage current, breakdown voltage and crystallographic x-ray measurements were conducted on the various wafers. Breakdown strength values were calculated from the breakdown voltage. In both groups of wafers, the measured thickness of a thin film with two layers was about 130 nm; with three layers, 180 nm; and, with five layers, 260 nm.

Figure 12:
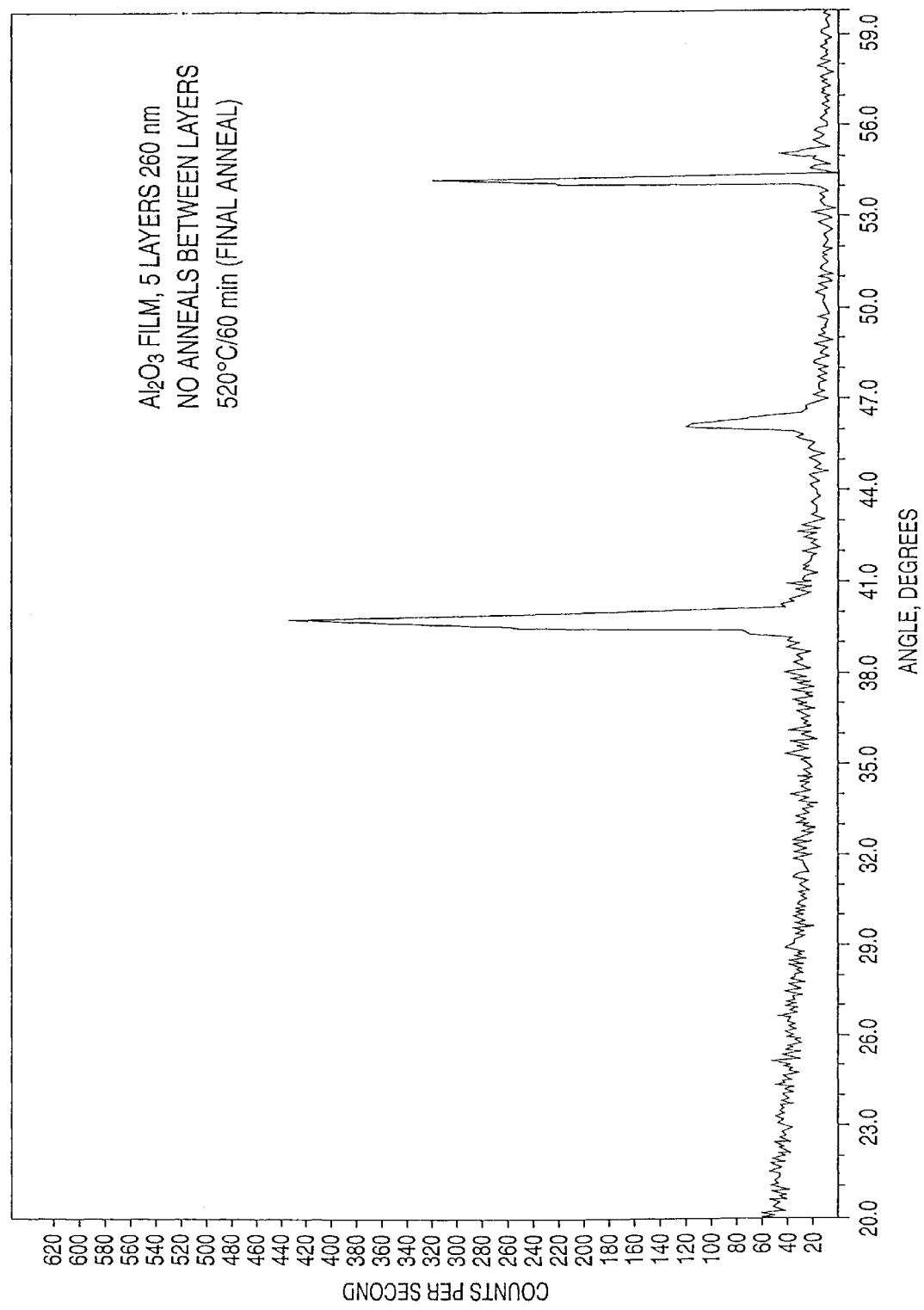
FIG. 12 depicts the results of a crystallographic x-ray analysis of a "bake-only" aluminum oxide thin film, fabricated without anneals between layers, conducted after the final anneal at 520° C.
Figure 13:
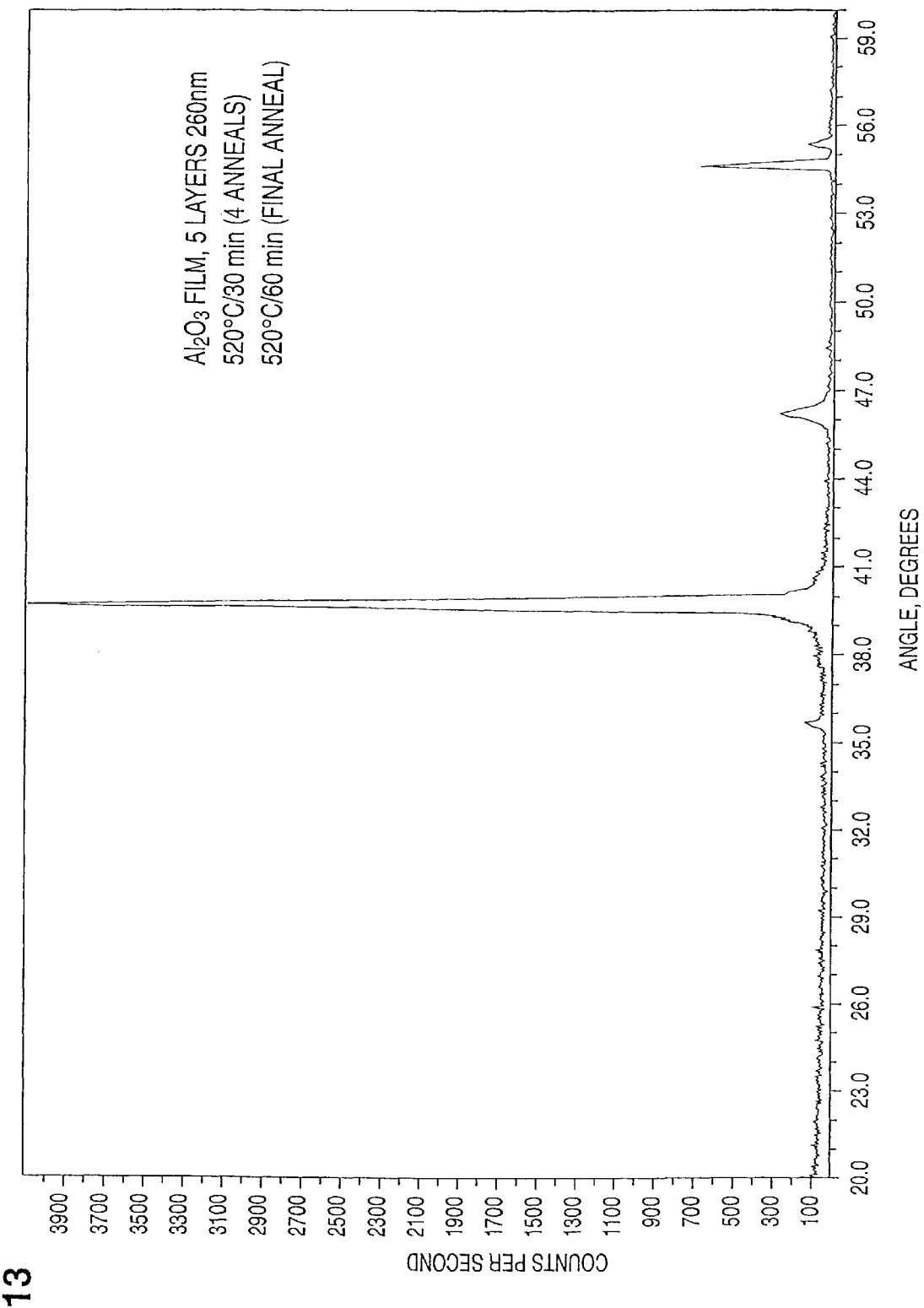
FIG. 13 depicts the results of a crystallographic x-ray analysis of an "anneal between layers" aluminum oxide thin film, fabricated with anneals for 30 minutes at 520° C. between layers, after the final anneal at 520° C.

FIG. 12 depicts the results of a conventional crystallographic x-ray analysis of a "bake-only" aluminum oxide thin film having five layers, fabricated without anneals between layers, after the final anneal at 520° C. The maximum value of the peak at 39.8 degrees is about 430 counts per second ("cps"), which is close to the corresponding value in the graph of FIG. 8, which was 250 cps. FIG. 13 depicts the results of a conventional crystallographic x-ray analysis of an "anneal between layers" aluminum oxide thin film having five layers, fabricated with anneals between layers, after the final anneal at 520° C. In FIG. 13, the maximum value of the peak at 39.8 degrees was about 4000 cps, that is, about ten times greater than the corresponding values in the graphs of FIGS. 8 and 12. Comparison of FIGS. 8, 12 and 13 indicates that the crystallographic peaks and, therefore, the crystal structures are similar in the thin films represented in FIGS. 8 and 12, and that the crystal structure represented in FIG. 13 is different from the other two. These observations suggest that low temperature annealing for 5 minutes at 350° C. between layers produces crystal structures resembling those from no annealing between layers. In contrast, annealing between layers at the higher temperature of 520° C. for 30 minutes produces crystal structures different from no annealing between layers.

Figure 14:
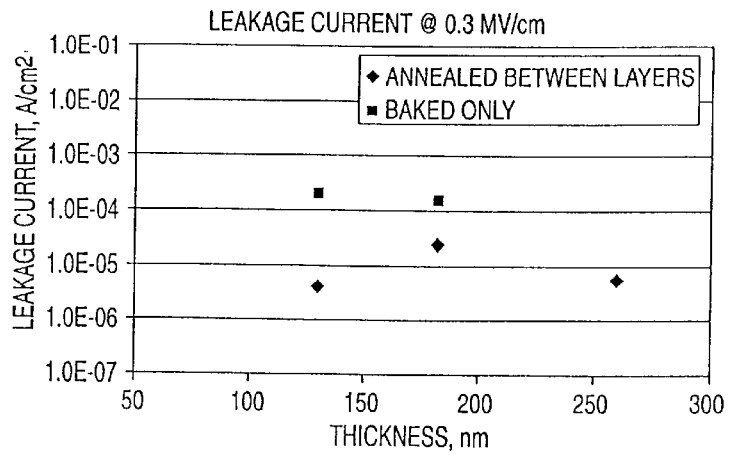
FIG. 14 is a graph of leakage current in units of $A/cm^2$, measured at 0.3 MV/cm and plotted as a function of film thickness, in nanometers, for the "baked-only" thin film and the "anneal between layers" thin films represented in FIGS. 12 and 13, respectively.
Figure 15:
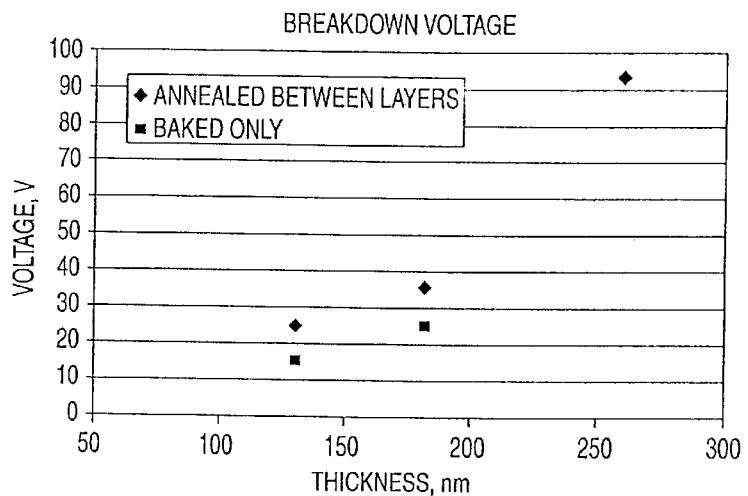
FIG. 15 is a graph of breakdown voltage, in volts, plotted as a function of film thickness of the thin films represented in FIG. 14.
Figure 16:
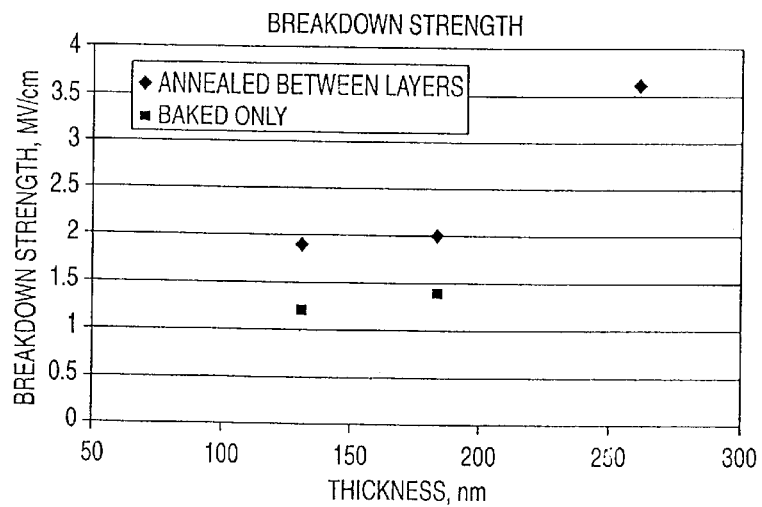
FIG. 16 is a graph of breakdown strength, in MV/cm, plotted as a function of film thickness of the thin films represented in FIGS. 14 and 15.

FIG. 14 is a graph of leakage current in units of $A/cm^2$, measured at 0.3 MV/cm and plotted as a function of film thickness, in nanometers, for "baked-only" thin films and "anneal between layers" thin films. FIG. 14 shows that the leakage current in "anneal between layers" thin films does not increase with increasing film thickness, and that the leakage current of the thin film having a thickness of 260 nm after the final anneal at 520° C. was $5.32 \times 10^{-6}$, measured at a field strength of 0.3 megavolts ("MV") per centimeter, typical of plasma display panels. This is an improvement over the results depicted in FIG. 9 for Example 3. In FIG. 15, breakdown voltage, in volts, is plotted as a function of film thickness. The data in FIG. 15 indicate that breakdown voltage increased with film thickness in the "anneal between layers" thin films, and it had a value of 94.8 volts at 260 nm. The value of 94.8 volts is an improvement over the value of 67.7 volts of Example 3, depicted in FIG. 10. The data in FIG. 15 were converted to values of breakdown strength, in MV/cm, and plotted as a function of film thickness in FIG. 16. The breakdown strength increased with film thickness and had a value of 3.65 MV/cm at 260 nm, which is an improvement over the value of 2.5 MV/cm of FIG. 11 in Example 3.

Examples 3 and 4 show how leakage current, breakdown voltage and other properties of aluminum oxide films may be improved by modifying anneal temperatures and anneal times during fabrication.

There has been described novel liquid precursors for fabricating aluminum oxide thin and thick film layers in integrated circuits, fluorescent lamps, and flat panel displays. The novel precursors are particularly useful for making transparent aluminum oxide thin films and thick films in fluorescent lamps, flat panel displays and other electrooptical devices. The novel precursors are used in metal organic decomposition techniques, in which an aluminum organic precursor containing one or more aluminum organic precursor compounds is applied to a substrate surface, where heat causes reaction and the formation of the desired aluminum oxide thin film or thick film layer. Selective combination of annealing time and temperature allows control of electrical properties. The invention, therefore, includes new compositions of, and methods of preparing, aluminum organic precursors. It should be understood that the particular embodiments shown in the drawings and described within this specification are for purposes of example and should not be construed to limit the invention, which will be described in the claims below. For example, the invention contemplates that the precursors of the invention may comprise a wide range of different types of aluminum organic precursor compounds that can be deposited and decomposed using metal organic decomposition techniques. Also, thin films and thick films made in accordance with the invention may comprise chemical compounds in addition to aluminum oxide. In particular, transparent films of electrooptical devices may comprise materials of various compositions and thicknesses. By selective treatment, thin films and thick films formed using the precursors of the invention may have different electrical properties, even if they have the same chemical composition. It is evident that those skilled in the art may now make numerous uses and modifications of the specific embodiments described, without departing from the inventive concepts. It is also evident that the steps recited may in some instances be performed in a different order; or equivalent structures and processes may be substituted for the structures and processes described. Consequently, the invention is to be construed as embracing each and every novel feature and novel combination of features present in and/or possessed by the liquid precursor compositions, liquid precursor preparation methods, and aluminum oxide film fabrication methods described.

What is claimed is:

1. A nonaqueous organic essentially final precursor for forming aluminum oxide, said essentially final precursor comprising a solution of an aluminum organic precursor compound dissolved in an organic solvent, wherein said aluminum organic precursor compound is selected from the group consisting of ethylhexanoate, octanoates, and neodecanoates.

2. A nonaqueous organic precursor as in claim 1 wherein said aluminum organic precursor compound comprises aluminum 2-ethylhexanoate.

3. A nonaqueous organic essentially final precursor for forming aluminum oxide, said essentially final precursor comprising a solution of an aluminum organic precursor compound dissolved in an organic solvent, wherein said organic solvent is selected from the group consisting of alcohols, aromatic hydrocarbons, and esters.

4. A nonaqueous organic essentially final precursor for forming aluminum oxide, said essentially final precursor comprising a solution of an aluminum organic precursor compound dissolved in an organic solvent, wherein said organic solvent is selected from the group consisting of xylenes, n-octane, 2-methoxyethanol, n-butyl acetate, 1,4-dioxane, methanol, methyl ethyl ketone, n-dimethylformamide, 2-methoxyethyl acetate, methyl isobutyl ketone, methyl isoamyl ketone, isoamyl alcohol, cyclohexanone, 2-ethoxyethanol, 2-methoxyethyl ether, methyl butyl ketone, hexyl alcohol, 2-pentanol, ethyl butyrate, nitroethane, pyrimidine, 1,3,5-trioxane, isobutyl isobutyrate, isobutyl propionate, propyl propionate, ethyl lactate, n-butanol, n-pentanol, 3-pentanol, toluene, ethylbenzene, 1-butanol, 1-pentanol, 2-pentanol, 1-hexanol, 2-hexanol, 3-hexanol, 2-ethyl-1-butanol, and 2-methyl-1-pentanol.

5. A nonaqueous organic precursor as in claim 4 wherein said organic solvent is n-octane.

6. A nonaqueous organic essentially final precursor for forming aluminum oxide, said essentially final precursor comprising a solution of an aluminum organic precursor compound dissolved in an organic solvent, wherein said organic solvent includes 2-ethylhexanoic acid.

7. A method of preparing an aluminum organic precursor solution having an aluminum organic precursor compound, comprising:
    mixing an aluminum alkoxide and a carboxylic acid in an organic solvent to form a reaction mixture, said aluminum alkoxide selected from the group consisting of methoxides, ethoxides, butoxides and pentoxides; and
    reacting said reaction mixture to form an aluminum carboxylate.

8. A method as in claim 7 wherein said aluminum alkoxide is s-butoxide.

9. A method of preparing an aluminum organic precursor solution having an aluminum organic precursor compound, comprising:
    mixing an aluminum alkoxide and a carboxylic acid in an organic solvent to form a reaction mixture, wherein said carboxylic acid is selected from the group consisting of 2-ethylhexanoic acid, octanoic acid, and neodecanoic acid; and
    reacting said reaction mixture to form an aluminum carboxylate.

10. A method as in claim 9 wherein said carboxylic acid is 2-ethylhexanoic acid.

11. A method of preparing an aluminum organic precursor solution having an aluminum organic precursor compound, comprising:
    mixing an aluminum alkoxide and a carboxylic acid in an organic solvent to form a reaction mixture, wherein said organic solvent is selected from the group consisting of xylenes, n-octane, 2-methoxyethanol, n-butyl acetate, n-dimethylformamide, 2-methoxyethyl acetate, methyl isobutyl ketone, methyl isoamyl ketone, isoamyl alcohol, cyclohexanone, 2-ethoxyethanol, 2-methoxyethyl ether, methyl butyl ketone, hexyl alcohol, 2-pentanol, ethyl butyrate, nitroethane, pyrimidine, 1, 3, 5-trioxane, isobutyl isobutyrate, isobutyl propionate, propyl propionate, ethyl lactate, n-butanol, n-pentanol, 3-pentanol, toluene, ethylbenzene, 1-butanol, 1-pentanol, 2-pentanol, 1-hexanol, 2-hexanol, 3-hexanol, 2-ethyl-1-butanol, 2-ethoxyethanol, and 2-methyl-1-pentanol; and
    reacting said reaction mixture to form an aluminum carboxylate.

12. A method as in claim 11 wherein said organic solvent is n-octane.

13. A method of preparing an aluminum organic precursor solution having an aluminum organic precursor compound, comprising:
    mixing an aluminum alkoxide and a carboxylic acid in an organic solvent to form a reaction mixture; and
    reacting said reaction mixture to form an aluminum carboxylate, wherein said aluminum carboxylate is selected from the group consisting of ethylhexanoates, octanoates, and neodecanoates.

14. A method as in claim 13 wherein said aluminum carboxylate is aluminum 2-ethylhexanoate.

15. A method of preparing an aluminum organic precursor solution having an aluminum organic precursor compound, comprising:
    mixing an aluminum alkoxide and a carboxylic acid in an organic solvent to form a reaction mixture, wherein said aluminum alkoxide comprises aluminum s-butoxide, said carboxylic acid comprises 2-ethylhexanoic acid, and said organic solvent comprises n-octane:
    reacting said reaction mixture to form an aluminum carboxylate.

16. A method of preparing an aluminum organic precursor solution having an aluminum organic precursor compound, comprising:
    mixing an aluminum alkoxide and a carboxylic acid in an organic solvent to form a reaction mixture; and
    reacting said reaction mixture to form an aluminum carboxylate, wherein said reacting comprises heating said reaction mixture at a temperature in the range of from 50° C. to 150° C. for a time period of from 6 hours to 30 hours.

17. A method of preparing an aluminum organic precursor solution having an aluminum organic precursor compound, comprising:
    mixing an aluminum alkoxide and a carboxylic acid in an organic solvent to form a reaction mixture;
    reacting said reaction mixture to form an aluminum carboxylate; and distilling said reaction mixture after said reacting.

18. A method as in claim 17 wherein said distilling is conducted at a temperature in the range of from 50° C. to 150° C.

19. A method as in claim 17 further comprising filtering said reaction mixture after said distilling.

20. A method as in claim 19 wherein said filtering is conducted through a 0.2 micron filter.

* * * * *

UNITED STATES PATENT AND TRADEMARK OFFICE
CERTIFICATE OF CORRECTION

PATENT NO.    : 6,495,709 B1                                    Page 1 of 1
DATED         : December 17, 2002
INVENTOR(S)   : Jolanta Celinska et al.

It is certified that error appears in the above-identified patent and that said Letters Patent is hereby corrected as shown below:

Title page,
Item [54], Title, delete "LIQUID PRECURSORS FOR ALUMINUM OXIDE AND METHOD MAKING SAME" and insert -- LIQUID PRECURSORS FOR ALUMINUM OXIDE AND METHOD OF MAKING SAME --

Column 14,
Lines 50 and 51, delete "group consisting of ethylhexanoate, octanoates, and neodecanoates." and insert -- group consisting of ethylhexanoates, octanoates, and neodecanoates. --

Signed and Sealed this

Twenty-fourth Day of June, 2003

JAMES E. ROGAN
*Director of the United States Patent and Trademark Office*